(12) United States Patent
Wiegand et al.

(10) Patent No.: US 10,048,128 B2
(45) Date of Patent: Aug. 14, 2018

(54) METHODS FOR COLLECTION, DARK CORRECTION, AND REPORTING OF SPECTRA FROM ARRAY DETECTOR SPECTROMETERS

(71) Applicant: Kaiser Optical Systems Inc., Ann Arbor, MI (US)

(72) Inventors: Patrick Wiegand, Pinckney, MI (US); James M. Tedesco, Livonia, MI (US); Joseph B. Slater, Dexter, MI (US); Francis Esmonde-White, Ann Arbor, MI (US); Darren Schipper, Ann Arbor, MI (US)

(73) Assignee: KAISER OPTICAL SYSTEMS INC., Ann Arbor, MI (US)

( * ) Notice: Subject to any disclaimer, the term of this patent is extended or adjusted under 35 U.S.C. 154(b) by 0 days.

(21) Appl. No.: 14/950,598

(22) Filed: Nov. 24, 2015

(65) Prior Publication Data
US 2016/0356647 A1 Dec. 8, 2016

Related U.S. Application Data

(63) Continuation-in-part of application No. 14/728,818, filed on Jun. 2, 2015.

(51) Int. Cl.
*G01J 3/02* (2006.01)
*G01J 3/44* (2006.01)
(Continued)

(52) U.S. Cl.
CPC ............ *G01J 3/0297* (2013.01); *G01J 3/027* (2013.01); *G01J 3/28* (2013.01); *G01J 3/44* (2013.01); *G01N 21/65* (2013.01)

(58) Field of Classification Search
CPC .. G01J 3/28; G01J 3/027; G01J 3/0297; G01J 3/44; G01N 21/27; G01N 21/65
See application file for complete search history.

(56) References Cited

U.S. PATENT DOCUMENTS

| 4,357,673 | A | * | 11/1982 | Willis | ................... G01D 1/14 |
| | | | | | 356/319 |
| 4,458,323 | A | * | 7/1984 | Willis | ................... G01D 1/14 |
| | | | | | 356/319 |

(Continued)

*Primary Examiner* — Kara E Geisel
*Assistant Examiner* — Violeta A Prieto
(74) *Attorney, Agent, or Firm* — John G. Posa; Belzer PC

(57) ABSTRACT

Methods and systems for spectrometer dark correction are described which achieve more stable baselines, especially towards the edges where intensity correction magnifies any non-zero results of dark subtraction, and changes in dark current due to changes in temperature of the camera window frame are typically more pronounced. The resulting induced curvature of the baseline makes quantitation difficult in these regions. Use of the invention may provide metrics for the identification of system failure states such as loss of camera vacuum seal, drift in the temperature stabilization, and light leaks. In system aspects of the invention, a processor receives signals from a light detector in the spectrometer and executes software programs to calculate spectral responses, sum or average results, and perform other operations necessary to carry out the disclosed methods. In most preferred embodiments, the light signals received from a sample are used for Raman analysis.

7 Claims, 10 Drawing Sheets

(51) Int. Cl.
*G01J 3/28* (2006.01)
*G01N 21/65* (2006.01)

(56) References Cited

U.S. PATENT DOCUMENTS

| | | | | |
|---|---|---|---|---|
| 4,891,772 A | * | 1/1990 | Case | G01S 7/4811 250/201.4 |
| 5,408,314 A | * | 4/1995 | Perry | G01J 1/44 348/E5.081 |
| 5,544,338 A | * | 8/1996 | Forslund | H04N 5/335 345/540 |
| 2012/0154655 A1 | * | 6/2012 | Compton | H04N 5/3658 348/308 |

* cited by examiner

METHODS FOR COLLECTION, DARK CORRECTION, AND REPORTING OF SPECTRA FROM ARRAY DETECTOR SPECTROMETERS

REFERENCE TO RELATED APPLICATION

This application is a continuation-in-part of U.S. patent application Ser. No. 14/728,818, filed Jun. 2, 2015, the entire content of which is incorporated herein by reference.

FIELD OF THE INVENTION

This invention relates generally to spectrometers and, in particular, to methods for collection, dark correction and reporting from such instruments.

BACKGROUND OF THE INVENTION

Electronic light-recording devices such as charge-coupled display (CCD) cameras, single element arrays, as found in InGaAs cameras, and so forth, have a dark response (i.e., a signal in the absence of light) which must be corrected. Normally this involves taking an exposure cycle in the absence of light from the sample to be measured and storing it as a "dark spectrum." Light from the sample is then passed to the camera for an identical exposure cycle to generate an "uncorrected sample spectrum." A "corrected" sample spectrum is then computed by subtracting the dark spectrum from the uncorrected sample spectrum. (Other forms of correction are then computed to correct for the spectral responsivity of the detectors, the spectral mapping of the array, interpolation, etc., but these are separate subjects outside the scope of this disclosure.) As the time between collection of the dark and the collection of light becomes larger, the dark data may not match the true camera response in the absence of light due to temperature fluctuation or other reasons.

If the dark spectrum is updated prior to each light exposure cycle, this essentially doubles the amount of time required for a total data collection cycle. Further, when analyzing spectra that contain both very weak and very strong spectral components of interest, the exposure cycle time required for adequate SNR (signal-to-noise)/quantitation on the very weak components, such as in analysis of gas mixtures by Raman spectroscopy, can be very long—on the order of several minutes. Stronger components in the same mixture may be accurately quantitated in a matter of seconds.

Previous attempts to solve the dark correction problem either are inefficient in the amount of time required, or inaccurate in matching the true dark response at the time of light collection. Existing techniques either collect one dark spectrum and apply it to all future spectra in an experiment or monitoring process, or collect a new dark spectrum before each signal spectrum.

Standard Practice 1

FIG. 1 illustrates current standard practice involving a single stored dark spectrum. A collection cycle consists of N accumulations of single exposures, each within the dynamic range of the array detector, summed or averaged to achieve a target SNR for the most difficult (typically the weakest) spectral feature in application. The resulting sum or average will henceforth be referred to as a spectrum A dark exposure is acquired with signal light blocked, thus acquiring one dark exposure at 102. A second dark exposure is acquired at 104 for cosmic event correction, and this process is repeated by summing or averaging the cosmic corrected exposures at 108 for N accumulations (106). In accordance with this disclosure, including the embodiments described here, "cosmic correction" should be taken to mean combining two (or more) exposures in such a way as to eliminate pixel signal if one of the exposures show evidence of cosmic ray spikes, while averaging the pixels from the both exposures if neither has a cosmic-ray-induced spike. Further, "N" is typically determined by the ratio of the strongest feature in the spectrum to the weakest feature, such that each of the N accumulations is sufficiently short to avoid detector saturation at the strongest feature, and the total exposure time T over N accumulations provides the required SNR for the weakest component.

The resulting dark spectrum is saved at 110 and subtracted at 112 from all subsequent signal collection spectra acquired in the same manner, but with signal light illuminating the detectors. The result is output at 114. This approach may comprise a standard practice for sufficiently stable dark current, which can be the case for very stable dark current, typically characterized by very stable thermal environments for both detector and spectrograph hardware. It can also be the case for applications with very strong signals relative to dark current. The cycle time for data within a run is the shortest possible because once the single dark spectrum is acquired, signal data is being acquired at all times. Total data reporting cycle time for the method of FIG. 1 is T, as dictated by the weakest component of interest.

Standard Practice 2

FIG. 2 illustrates an alternative standard practice involving interleaved dark spectra. A dark spectrum is acquired at 202, followed by the acquisition of signal spectra at 204. The dark signal is subtracted from the light spectrum at 206. A new dark spectrum is acquired over N accumulations as described above in between each signal cycle of N accumulations. This allows the instrument to correct for changes in dark current over the course of a data run. However, it doubles the data cycle time relative to Standard Practice 1, because half of the time is spent acquiring dark spectra, not signal. Thus, total data reporting cycle time is 2T.

SUMMARY OF THE INVENTION

This invention is directed to a system and method of dark current correction in a spectrometer having a detector adapted to receive light from a sample. The overall goal is to provide for efficient dark correction while keeping the total data collection cycle to a minimum. The various embodiments also enable more rapid reporting of data than that which would normally be dictated by accurate quantitation of the weakest signal of interest.

The invention affords better matching of dark subtraction to the true dark when light data is acquired. This results in more stable baselines, especially towards the edges where intensity correction magnifies any non-zero results of dark subtraction, and changes in dark current due to changes in temperature of the camera window frame are typically more pronounced. The resulting induced curvature of the baseline makes quantitation difficult in these regions.

One disclosed method allows dark data to be pre-calibrated during extended periods of time to improve the accuracy and reduce noise, then these calibrations can be used at any point in the future without incurring an increased measurement time. Alternative methods provide additional metrics for the identification of system failure states such as loss of camera vacuum seal, drift in the temperature stabilization, and light leaks.

In system aspects of the invention, a processor receives signals from a light detector in the spectrometer and executes software programs to calculate spectral responses, sum or average results, and perform other operations necessary to carry out the disclosed methods. In most preferred embodiments, the light signals received from a sample are used for Raman analysis.

DETAILED DESCRIPTION OF THE INVENTION

Method 1—Interleaved Dark Exposure

Figure 3:
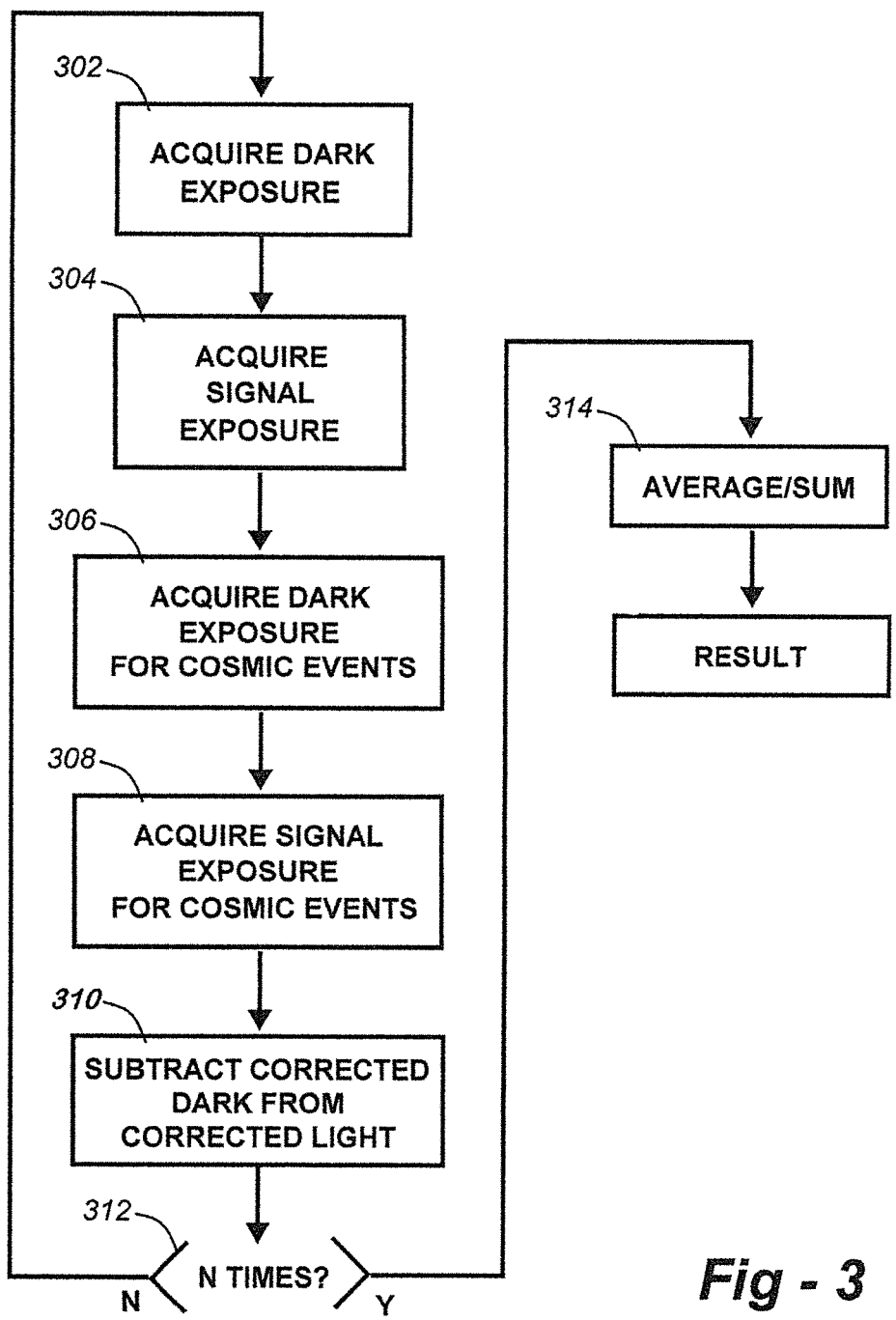
FIG. 3 illustrates an interleaved dark exposure method according to the invention.

In accordance with this embodiment of the invention, diagrammed in FIG. 3, a collection cycle comprises dark exposure 302, light exposure 304, repeat dark for cosmic correction check 306, repeat light for cosmic correction check 308, and generate one accumulation by subtracting the cosmic-corrected dark exposure from the cosmic-corrected light exposure (310). These steps are repeated N times through decision block 312 for each accumulation. At 314 the accumulations are summed or averaged to build up the target SNR for the application.

This improvement doubles the fastest possible cycle time and better matches the true dark for light collection periods to the stored dark as compared to Standard Practice 2. This can be significant in applications where dark current can drift significantly within a long single data cycle of N accumulations. Data reporting cycle time is 2T, equivalent to Standard Practice 2, but provides more accurate tracking of dark current drift than Standard Practice 2.

Method 2—Rolling Collection

Figure 4:
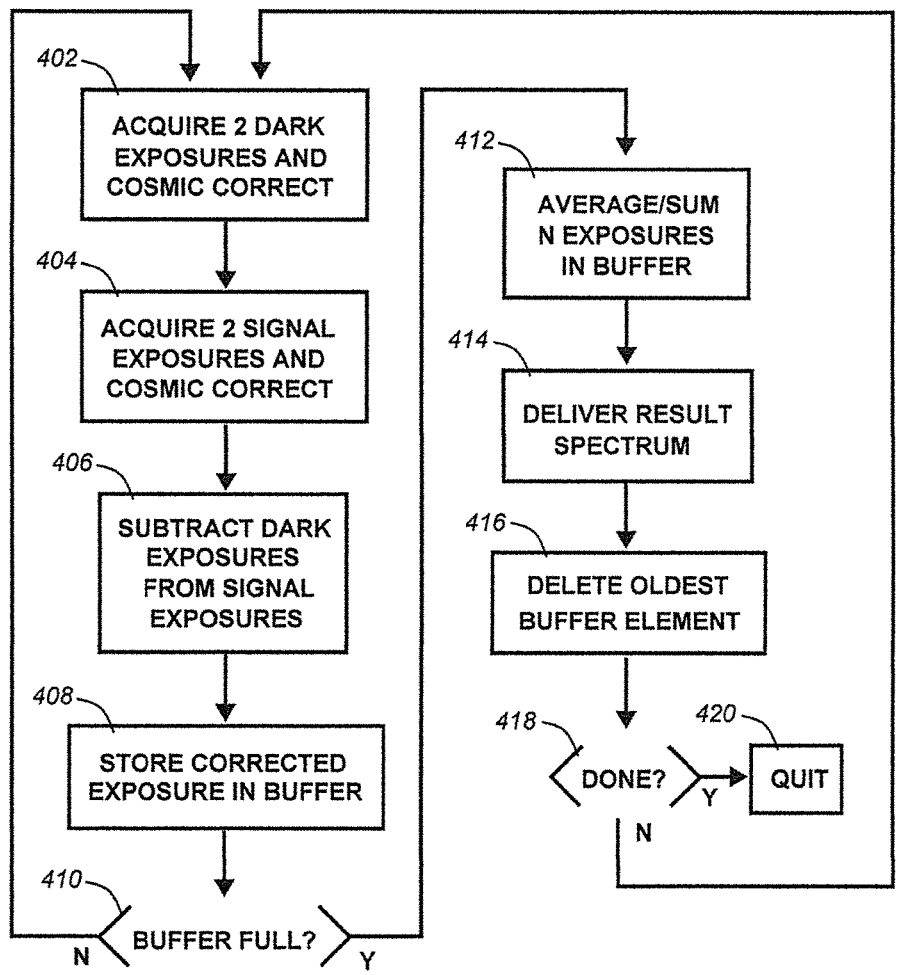
FIG. 4 illustrates a rolling collection method according to the invention.

In the embodiment of FIG. 4, the acquisition cycle includes performing Interleaved Dark Exposures of FIG. 3 for each accumulation, storing each of the N accumulations in a buffer. Two dark exposures are collected and cosmically corrected at 402; two light exposures are collected and cosmically corrected at 404; with the difference 406 being stored in a buffer at 408. When desired number of exposures N has occurred (at 410), a sum or average is taken at 412 a first collect cycle spectrum result is returned at 414, and the oldest buffer element is deleted. Steps 402-408 are repeated through 416, and the result of each corrected exposure is added to the buffer as newest buffer element. Another collect cycle spectrum is returned which incorporates all buffer elements including the newest one.

This process is repeated as a rolling sum or average spectrum delivery until a sufficient number of spectra has been achieved via block 418, in which case the process quits at 420. Although full reaction to a step change in signal level is similar to Standard practice 2, data reporting to indicate the onset of a signal change is actually faster than the cycle time of Standard Practice 1, returning a new spectrum with the target SNR on every accumulation, instead of every N accumulations. The data reporting cycle time is now 2T/N (except for the first spectrum which would be delivered after 2T).

Method 3—Dynamically Modeled Dark Collection

Figure 5:
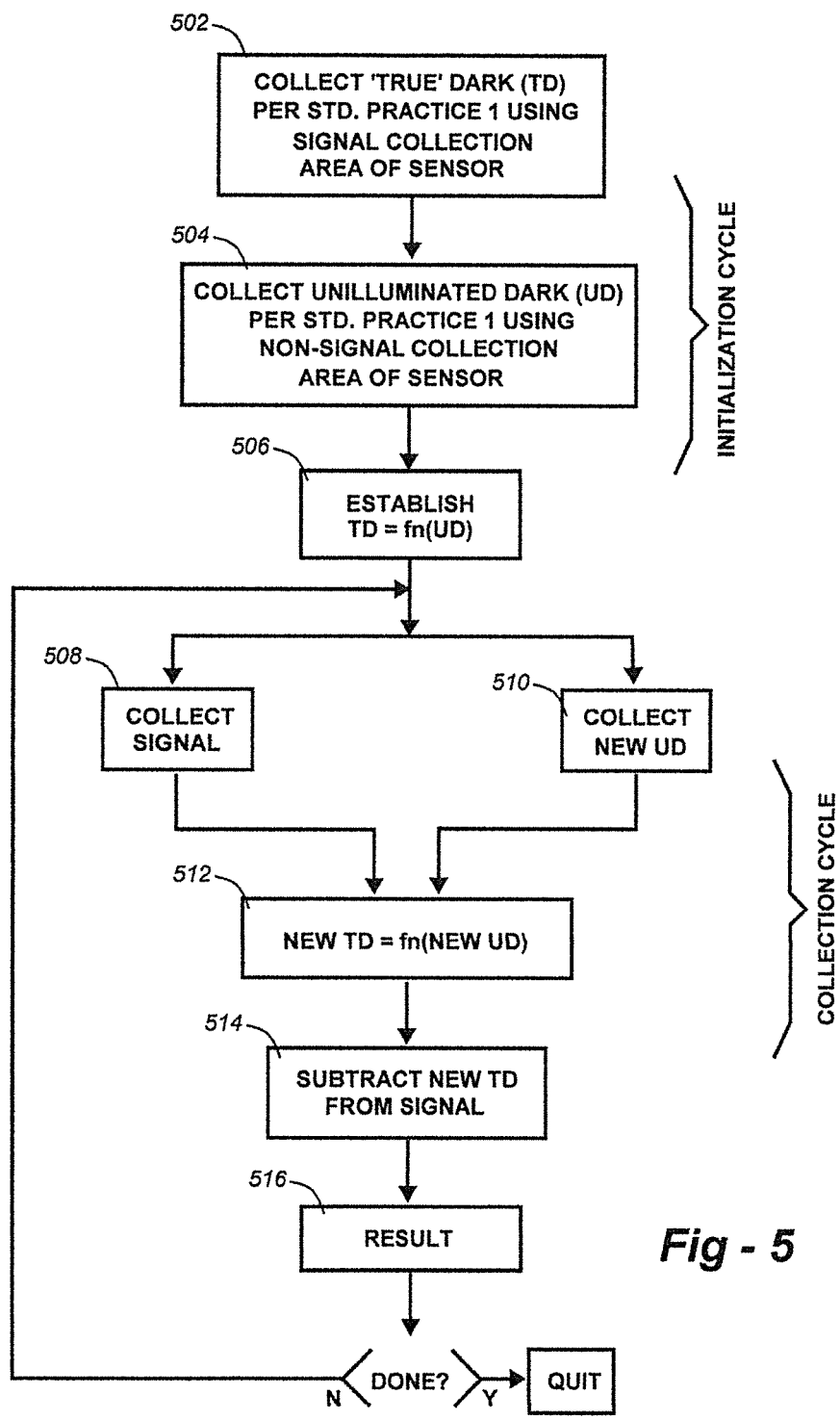
FIG. 5 illustrates a scaled dark collection method according to the invention.

In accordance with the embodiment of FIG. 5, a dark is collected at the beginning of an experiment at 502 using the entire data collection cycle and stored as in Standard Practice 1. This dark uses the same region of the camera as light collection, but with no light entering the camera, and will be referred to as the true dark (TD). Subsequently, a second dark is collected at 504 using regions of the camera not normally illuminated during signal collection, such as in between signal fiber images on a 2-dimensional CCD array, or non-illuminated regions of a linear array detector. This dark is collected with light entering the camera and will be referred to as the unilluminated dark (UD).

At 506, a relationship is developed dynamically between the TD and UD, indicated as TD=fn(UD). In some situations the functions may simply be a multiplication by constant. A light collection cycle is then started at 508. Simultaneously, another UD is collected at 510 using detector regions not illuminated by signal light. Using the previously developed relationship between the TD and the UD, a new TD is calculated at 512 using the monitored UD signal. The calculated TD is then subtracted from the signal exposure at 514. The result at 516 should closely match the signal corrected by true dark during light collection. No additional exposure time is required.

Data reporting cycle time after initial dark collection is T, which is equivalent to Standard Practice 1. Drifting dark current is now corrected, although not as accurately as with the Rolling Collection approach. If the dark current drift is reasonably consistent across the detector array, this can provide sufficiently accurate correction. A new relationship between the TD and the UD is developed each time the experimental parameters (such as time of exposure or detector temperature) change. No additional inputs to the function relating TD and UD are necessary other than the UD.

Note that in this method, the initial dark may be taken for a subset of total accumulations to save start-up time, but this would compromise SNR. Also, the UD does not have to be a contiguous stripe across the camera but can in fact be any collection of unilluminated pixels.

Method 4—Combination of Methods 2, 3

Figure 6:
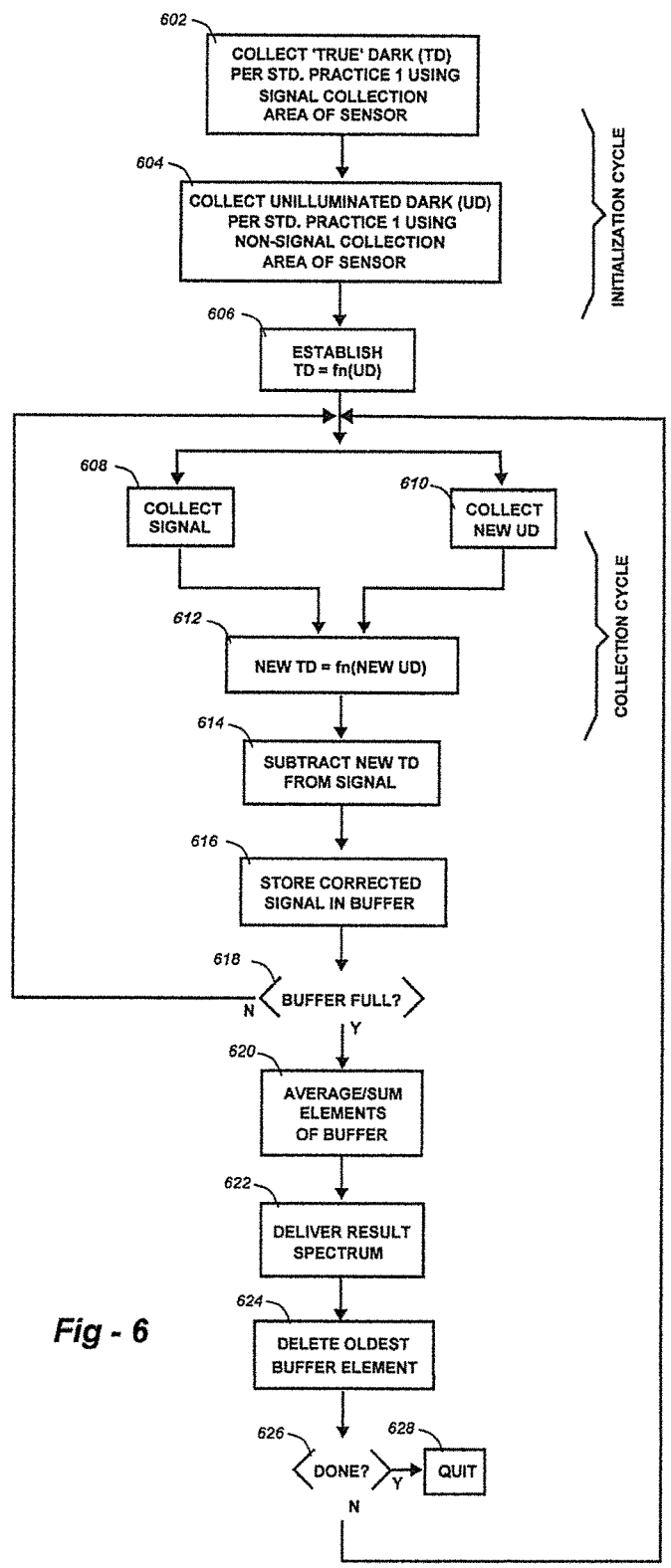
FIG. 6 illustrates an embodiment of the invention that combines the Methods depicted in FIGS. 4 and 5.

The approach of FIG. 6 essentially combines the improved Methods 2 and 3 (FIGS. 4 and 5). The technique represents a rolling collection of both signal and dynamically modeled TD correction, reporting data on every signal accumulation without interleaved dark collections. Blocks 602, 604 and 606 are equivalent to the initialization cycle of FIG. 5, and blocks 608, 610, 612 representing the collection cycle. At 614 the dark is subtracted from the signal and the result being stored in a buffer at 616. As with the process of FIG. 4, when desired number of accumulations N has occurred (at 618), a sum or average is taken at 620, a first collect cycle spectrum result is returned at 622, and the oldest buffer element is deleted at 624. Steps 608-624 are repeated through 626, and the result of each accumulation is added to the buffer as newest buffer element. Another collect cycle spectrum is returned which incorporates all buffer elements including the newest one. The data reporting cycle time is T/N—Twice the speed of Rolling Collection Method 2.

Method 5—Statically Modeled Dark Correction

For cameras with a consistent dark current vs. detector temperature characteristic, the complete dark spectrum response to relevant parameters, such as integration time and detector array temperature, can be measured over the entire array and stored once in advance at select intervals within the expected operational ranges. These parameters can then be measured during operation, and the expected operational dark signal calculated via interpolation of the stored data. This provides the advantage of low noise dark current subtraction, with the operational simplicity of Standard Practice 1, although a new static model would have to be developed for each instrument at the time of manufacture or refurbishment.

Figure 7:
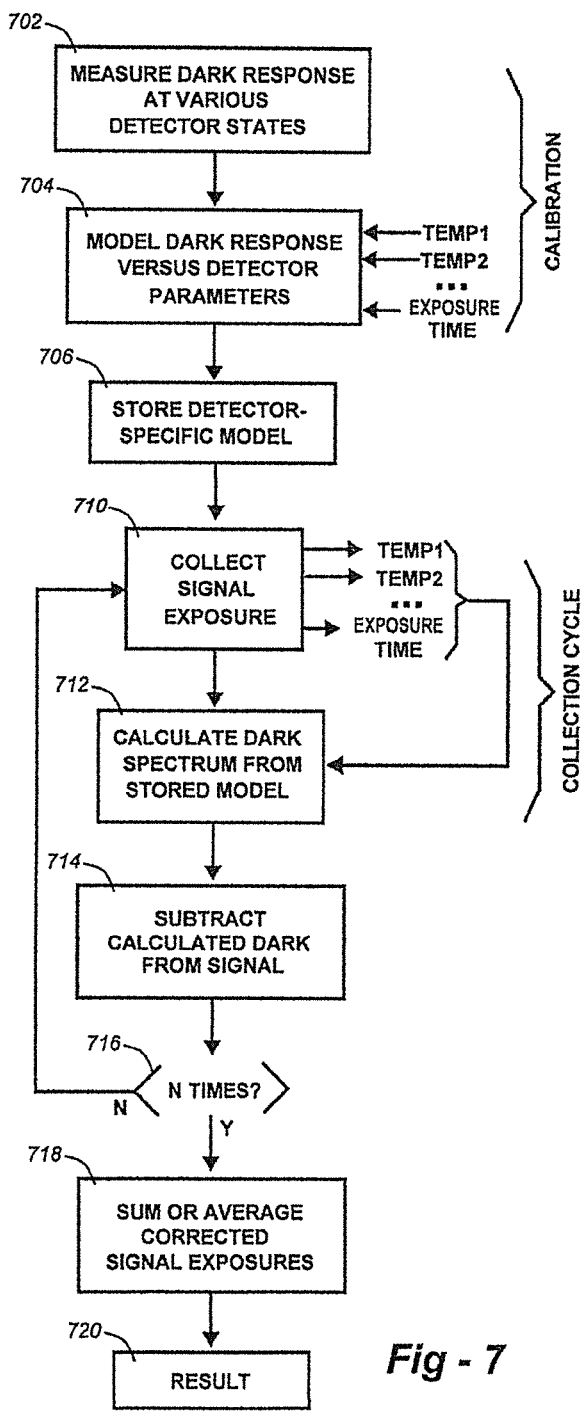
FIG. 7 illustrates a calculated full spectrum dark correction method according to the invention.

The technique is diagrammed in FIG. 7. At 702, dark response is measured at various detector states. At 704, dark response is measured in conjunction with various detector parameters such as different temperatures, exposure time(s), and so forth. The responses acquired at 702, 704 are stored at 706 as a specific model for that particular detector.

The collection cycle begins at 710, wherein the signal spectrum is collected along with the state and parametric information derived at 702, 704. This allows the dark spectrum to be calculated using the stored model at 712. The calculated dark is subtracted from the signal at 714 and this is repeated N times via 716. The corrected signal exposures are summed or averaged at 718 and the result delivered at 720. Data reporting cycle time can be either T or T/N, depending on the incorporation of the rolling average method described in Method 4.

Method 6—Scale-Enhanced Statically Modeled Dark Correction

Figure 8:
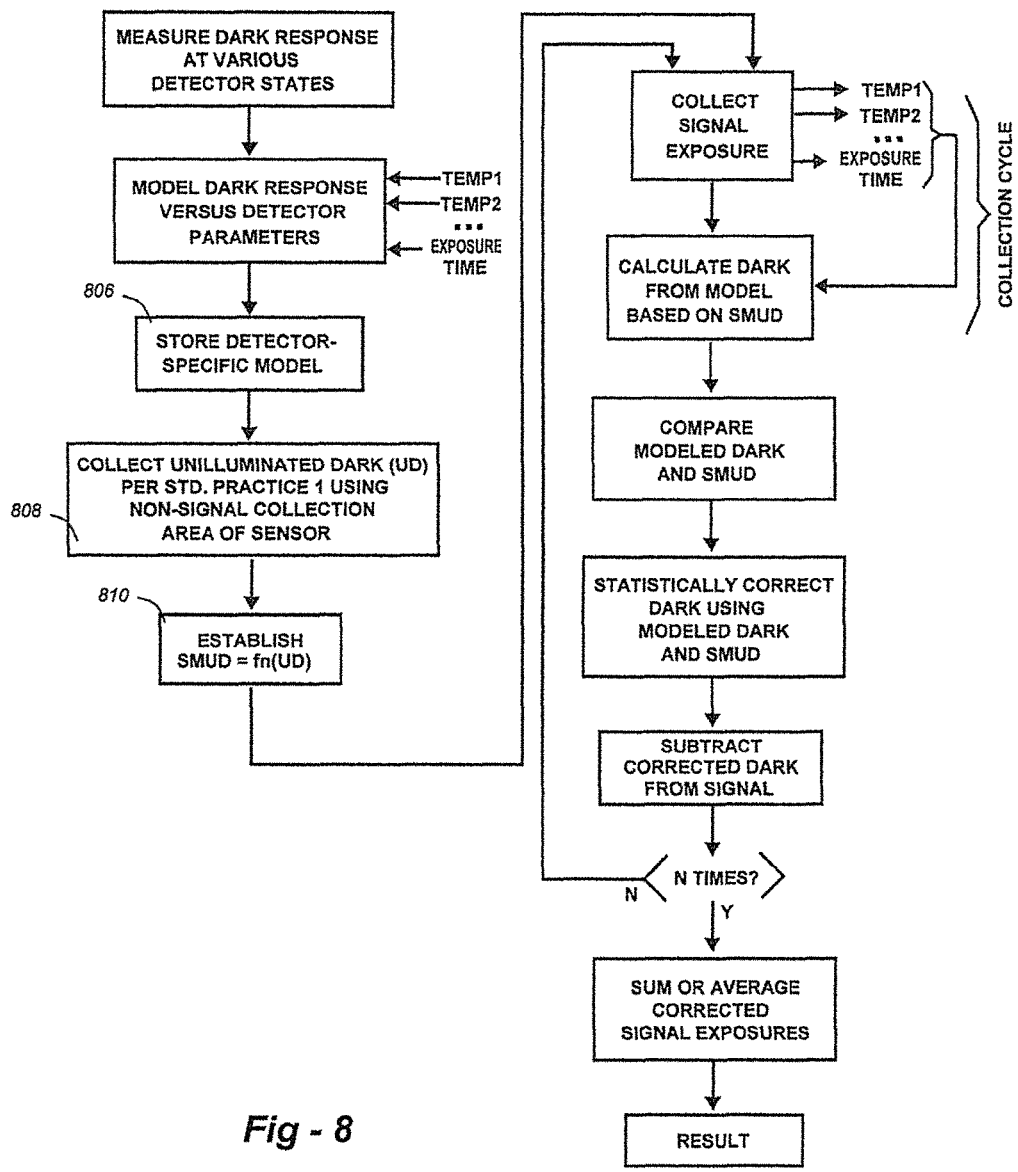
FIG. 8 illustrates an embodiment of the invention that combines the Methods depicted in FIGS. 5 and 7.

The embodiment of the invention shown in FIG. 8 represents a combination of Methods 3 and 5. As in Method 5, a functional relationship is developed at 806 between true dark (TD) and relevant operational parameters (e.g., integration time, array temperature). In addition, another functional relationship is developed at 810 between unilluminated dark at 808 (where light is entering the camera but not falling on the UD regions) and the operational parameters used in the first functional relationship. This will be referred to as statically modeled unilluminated dark (SMUD). As in Method 5, these functional relationships would be developed at the time of instrument manufacture or refurbishment and used for all future correction of exposures where signal light is illuminating the detector regions.

In this embodiment, however, the statically modeled dark correction is supplemented with a scaled dark correction factor determined from the difference between the actual UD that is measured and the UD that is predicted from the statically modeled unilluminated dark. This accounts for camera instability or other operational variables not accounted for in the implementation of Method 5. This process includes statistical measures to determine when the UD region differs significantly from the calculated UD value, in turn triggering the application of an additional scaled dark correction to supplement the statically modeled dark function. This approach can also provide additional benefits, such as correcting for interchannel smearing in shutter-free applications and handling unexpected light leakage inside the spectrograph.

Data reporting cycle time can be either T or T/N depending on the incorporation of the rolling average method described in Method 4.

Selection of N Based on External Control System Requirements

As described above, the total number of accumulations N is typically related to the ratio of the strongest signal to the weakest signal in the spectrum in order to avoid detector saturation on any single accumulation. Improved methods 2 and 4 shorten the data reporting cycle to 2T/N or T/N respectively. However, some applications may need still faster reporting cycles to support control system requirements. An example of such an application would be optimizing the efficiency of a natural gas turbine power generator based on the varying concentrations of different hydrocarbon constituents in the gas being fed to the generator. In improved methods 2 and 4, the required signal exposure time T may be divided in to a larger number of accumulations N in order to report at a speed consistent with the control application. The number N will be limited at some point by increasing relative significance of detector read noise and A/D quantization noise, as understood to those of skill in the art.

Component Selective Response Time

Improved methods 2 and 4 above provide more rapid indications of an onset changes in sample constituents than standard practice. However, they still nominally require time 2T or T, respectively, to fully respond to a step change in the sample. Methods 2 and 4 may be further modified such that the stronger spectral components are assigned buffer sizes that are smaller than the N accumulations as described in Method 2. As described above, T is dictated by the weakest component in the spectrum, whereas stronger constituents can achieve a target SNR in a shorter total exposure time. By customizing the buffer size to be smaller than N as appropriate for stronger spectrum components, detector-by-detector, the system can be made to fully respond to changes in concentration on stronger components more rapidly.

Bracketed Dark Methods

Figure 9:
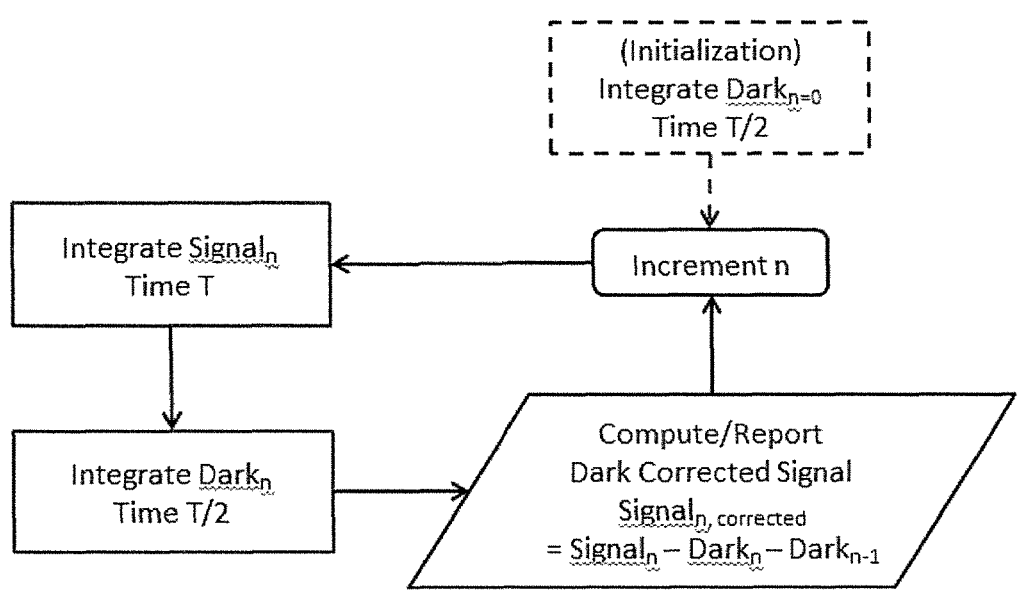
FIG. 9 is a simplified flow diagram that depicts a bracketed dark method.

It has been discovered that additional advantages may be gained by acquiring multiple dark and multiple signal exposures, but splitting the dark collections so that half are taken before the signal exposures, and half are taken after the signal exposures. The total dark is then subtracted from the signal to produce a "collection." This has two advantages. First, by splitting the darks into two halves that bracket the signal, the dark spectrum better matches the true dark contribution to the bracketed signal collection. A second advantage is that the ending dark half-series of one collection is re-used as the beginning half-series of darks for the following collection, thus saving time. For equivalent total number of darks to signal exposures, the data cycle time drops from 2T to 1.5T, as shown conceptually in FIG. 9.

In practice, each time interval of dark and signal integration may be a summation or average of multiple camera exposures/readouts. This is often necessary in order to acquire a target Signal to Noise Ratio (SNR) on spectral features that might otherwise be too weak, as limited by the dynamic range of the camera, the dark current of the camera, and/or stronger signals in the spectrum.

It is also standard practice to apply "cosmic filtering" to each exposure of dark and signal. This process splits a desired exposure interval into two equal sub-intervals. The two sub-intervals are compared with each other to detect any anomalous high-intensity "spikes" in one of the two spectra. These spikes occur as random low-probability cosmic radiation events, and discarded when detected. Any reference to an "exposure" below may also in practice be cosmically filtered data acquired in this way.

Note that the number of dark exposures does not necessarily have to match the number of signal exposures if the noise inherent in the dark exposure is not a substantial contributor to the total noise inherent in the collection. This would be the case in a scenario where the dark current is much lower than the signal current. In such a scenario, additional time gains can be made by using less total dark exposures than signal exposures, providing signal to noise of the resulting collection is still adequate. In this case the shorter dark exposures can be scaled to compensate for the different total integration time relative to the signal exposures, yielding an "effective integration time" of T/2 according to FIG. 9.

Figure 1:
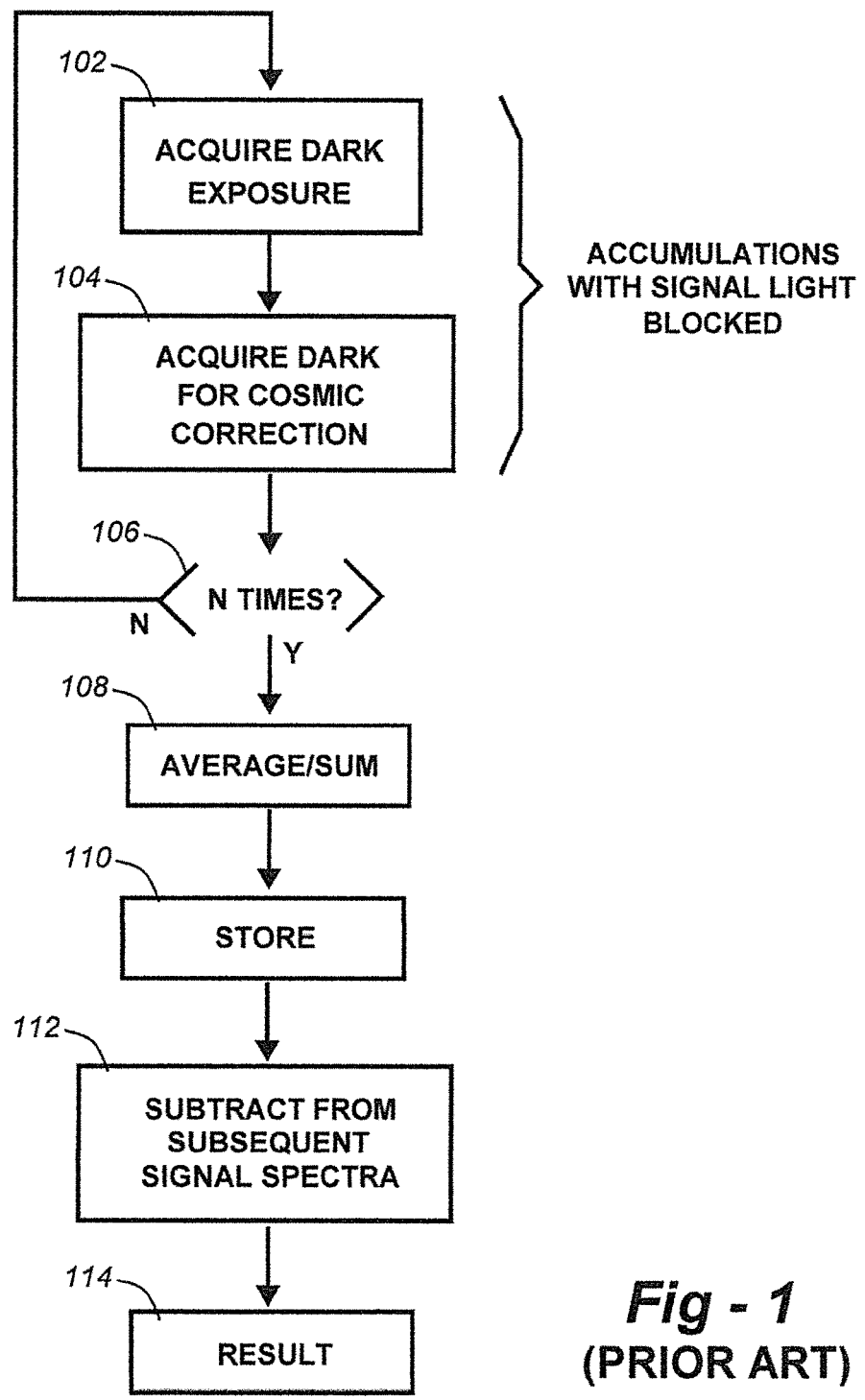
FIG. 1 is a diagram that illustrates a current standard practice involving a single stored dark spectrum.
Figure 2:
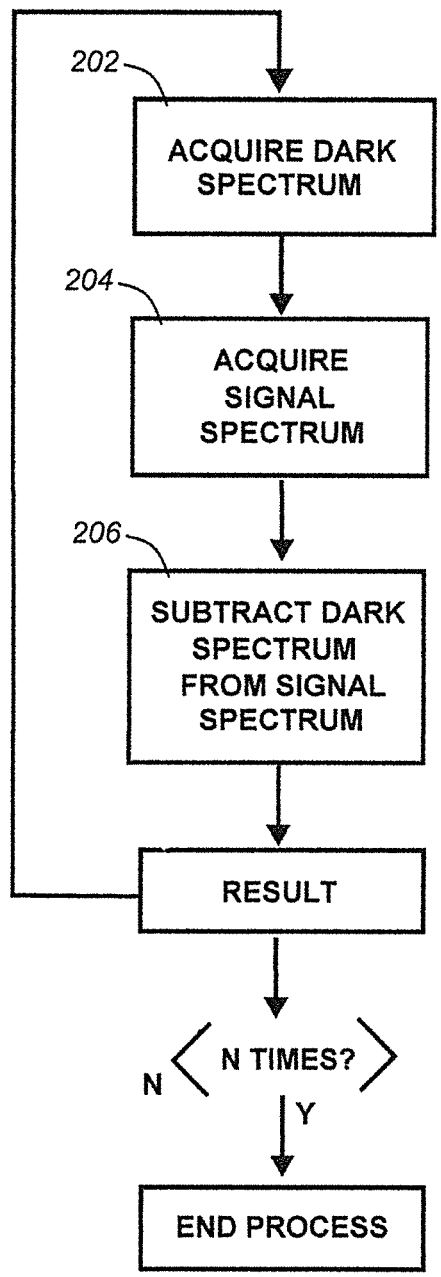
FIG. 2 illustrates an alternative standard practice involving interleaved dark spectra.
Figure 10:
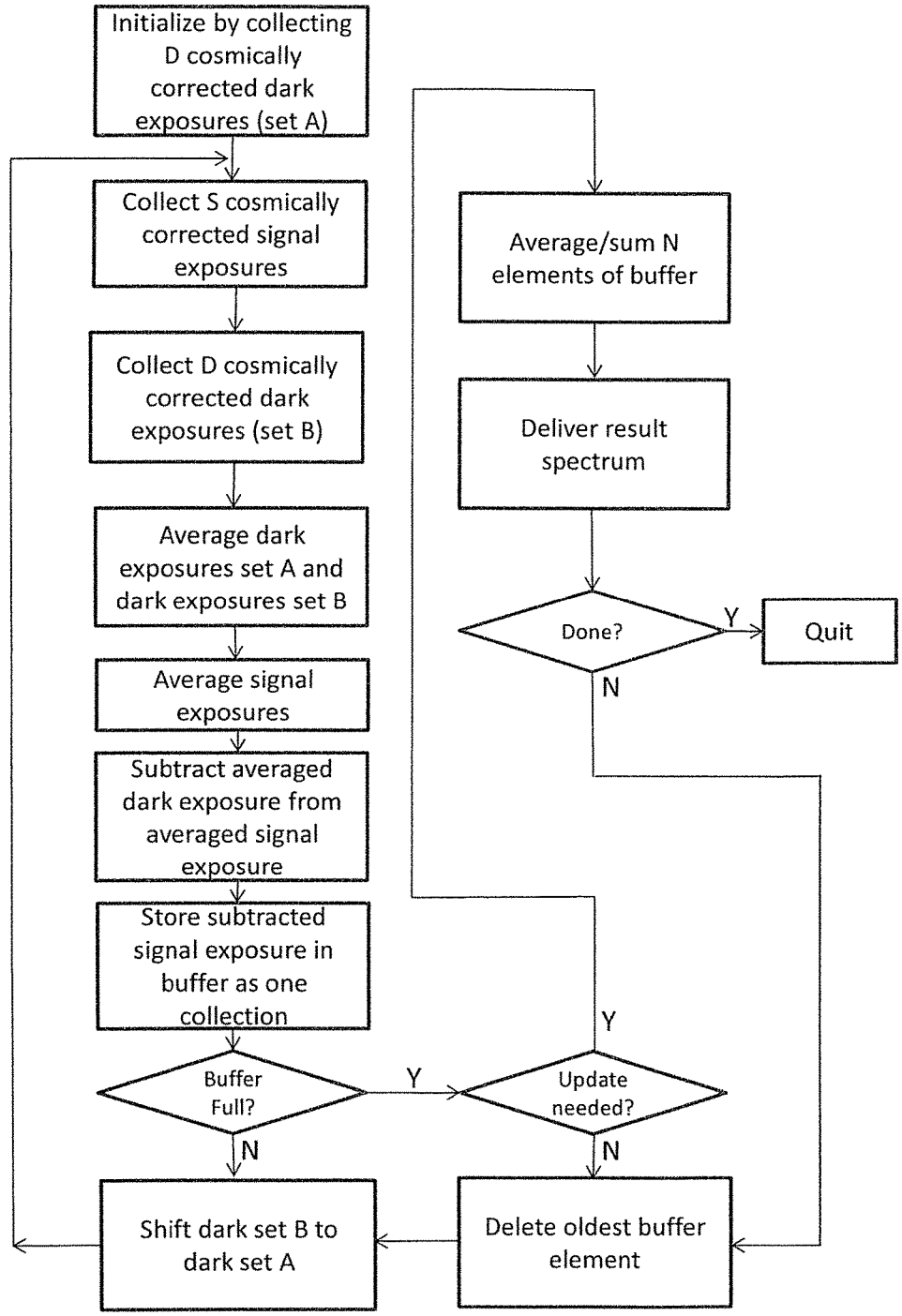
FIG. 10 is a detailed flow diagram of a bracketed dark method.

This bracketed dark method is applicable to any embodiment disclosed herein where multiple dark and signal collections are performed in order to achieve a desired signal-to-noise ratio. Indeed, this modification is applicable to the Standard Practice of FIG. 2. This improvement is also applicable to the embodiments that employ a buffer. By defining a "collection" as one corrected averaged/summed signal exposure, each collection is placed in a buffer which can then be used to return averaged or summed collections as a spectrum on a rolling basis (FIFO buffer). To demonstrate, the modification is applied to Method 2, the "Rolling Collection" method shown in FIG. 4, with the modified version being depicted in FIG. 10. A detailed description of FIG. 10 proceeds as follows:

1. First a series of D cosmically corrected dark exposures are collected. Call this set A.
2. A set of S cosmically corrected signal exposures (shutter open) are then collected. D will typically be ½ S but may also be less, down to the case where D=1.
3. A second set of D cosmically corrected dark exposures are obtained.
4. The two sets of dark exposures (set A and set B) are then averaged or summed. If they are summed, and 2D does not equal S, then a scaling of the dark sum by multiplying by S/2D would occur so that the sum is then appropriate for S exposures.
5. The set of signal exposures are then averaged or summed.
6. The average/sum of the signal exposures is then corrected by subtracting the average/sum of the dark exposures.
7. The subtracted signal exposure, subsequently referred to as one "collection" is stored in a buffer of length N.
8. Steps 2-7 are repeated more times until the buffer is full. At this time the first spectrum is constructed by averaging/summing the N buffer elements.
9. The oldest element in the buffer is discarded. Also the set of darks previously referred to as set B now become set A and the former set A is discarded.
10. Steps 8-9 are repeated, again filling the buffer. At this point another spectrum can be delivered, or the buffer further updated. The update interval (how many times the buffer is shifted by repeating steps 8 and 9) can vary from 1 (fastest update time, deliver a spectrum after every collection) to N (slowest update time, no rolling average/sum occurs).

This cycle continues until no further spectra are desired.

Method Selection Based on Application

The selection of a method described herein depends on timing, accuracy, setup/computational resource priorities and application requirements. Interleaved dark collection above is the most accurate way to track dark current, particularly for single row cameras with high and significantly varying dark current such as an InGaAs linear array camera, and also the most accurate way for a 2D array camera such as a CCD, providing both increased data reporting rate at target SNR, and most accurate correction for varying dark current. The Standard Practice of a single dark collection is a faster, providing twice the data/response rate in return for a less rigorous estimated tracking of dark current. The Statistically Modeled Dark correction is the fastest overall method (including manufacturing time and end-user time), as it requires no additional effort at time of manufacture. However, this method provides still faster reporting of data from the viewpoint of the customer, although the customer may have to pay a charge for developing the model as extra work is required at time of manufacture. Finally, several of the methods can benefit by implementation as a rolling average, if demanded by a process control system, without actually changing the amount of time for the system to fully respond to a step change in the process constituents. Finally, customization of the amount of averaging based on process control requirements or component concentration can also be employed.

The invention claimed is:

1. A method of dark current correction in an instrument having a detector adapted to receive a dark exposure and a light spectrum from a sample, the method comprising the steps of:
   (a) collecting a first set A of dark exposures with an exposure time D;
   (b) collecting a first set of of signal exposures with an exposure time S;
   (c) collecting a second set B of dark exposures with an exposure time D; wherein D represents a total exposure time of equal to or less than that of S/2;
   (d) averaging or summing the results of (a) and (c), and scaling the result for an equivalent total dark exposure time equal to S;
   (e) averaging or summing the result of (b); and
   (f) subtracting the result of (d) from the result of (e) to deliver a dark-corrected collection;
   (g) storing the result of (f) in a first-in/first-out buffer having N buffer elements;
   (h) discarding set A and renaming set B as set A to re-use at least a portion of the dark exposure;
   (i) repeating steps (b) through (g) until the buffer is full and, if a sample spectrum is desired:
   (j) averaging or summing the N buffer elements to output the sample spectrum or, if a sample spectrum result is not desired:
   (k) discarding the oldest element in the buffer and returning to step (h).

2. The method of claim 1, including the step of repeating steps (b) through (f) until a desired signal-to-noise ratio is achieved by summing or averaging the multiple dark-corrected collections from (f).

3. The method of claim 1, wherein the spectrometer is a Raman spectrometer, and the sample spectrum is a Raman spectrum.

4. The method of claim 1 wherein, in step (f), the dark-corrected collection is obtained by bracketing the light spectrum on both sides.

5. The method of claim 1, wherein step (k) is repeated to improve the accuracy of the sample spectrum.

6. The method of claim 5, wherein a sample spectrum is delivered after every dark-corrected collection.

7. The method of claim 5, wherein a sample spectrum is not delivered after every dark-corrected collection.

* * * * *